United States Patent
Suzuki et al.

(10) Patent No.: US 10,118,899 B2
(45) Date of Patent: Nov. 6, 2018

(54) PRODUCTION METHOD OF ENZALUTAMIDE CRYSTAL FORM

(71) Applicant: Astellas Pharma Inc., Tokyo (JP)

(72) Inventors: Yusuke Suzuki, Tokyo (JP); Shuichi Nakagawa, Tokyo (JP); Tsuyoshi Kitamura, Tokyo (JP)

(73) Assignee: Astellas Pharma, Inc., Tokyo (JP)

( * ) Notice: Subject to any disclaimer, the term of this patent is extended or adjusted under 35 U.S.C. 154(b) by 0 days.

(21) Appl. No.: 15/577,007

(22) PCT Filed: May 27, 2016

(86) PCT No.: PCT/JP2016/065729
§ 371 (c)(1),
(2) Date: Nov. 27, 2017

(87) PCT Pub. No.: WO2016/194813
PCT Pub. Date: Dec. 8, 2016

(65) Prior Publication Data
US 2018/0148417 A1    May 31, 2018

(30) Foreign Application Priority Data
May 29, 2015 (JP) .................................. 2015-109805

(51) Int. Cl.
C07D 233/86 (2006.01)
C07C 331/28 (2006.01)
C30B 7/00 (2006.01)
C30B 33/00 (2006.01)

(52) U.S. Cl.
CPC .......... *C07D 233/86* (2013.01); *C07C 331/28* (2013.01); *C30B 7/00* (2013.01); *C30B 33/00* (2013.01)

(58) Field of Classification Search
CPC .................................................. C07D 233/86
See application file for complete search history.

(56) References Cited

U.S. PATENT DOCUMENTS

| | | |
|---|---|---|
| 9,174,943 B2 | 11/2015 | Jain et al. |
| 9,701,641 B2 | 7/2017 | Peddy et al. |
| 2013/0190507 A1 | 7/2013 | Jain et al. |
| 2015/0210649 A1 | 7/2015 | Dwivedi et al. |

FOREIGN PATENT DOCUMENTS

| | | |
|---|---|---|
| CN | 104610158 A | 5/2015 |
| WO | 2011/106570 A1 | 9/2011 |
| WO | 2014/041487 A2 | 3/2014 |
| WO | 2015/054804 A1 | 4/2015 |
| WO | 2016/005875 A1 | 1/2016 |

OTHER PUBLICATIONS

Search report for PCT/JP2016/065729, 2 pages, dated Aug. 23, 2016.

*Primary Examiner* — Joseph R Kosack
*Assistant Examiner* — Karen Cheng
(74) *Attorney, Agent, or Firm* — Banner & Witcoff, Ltd.

(57) ABSTRACT

The present invention aims to provided a novel production method of an enzalutamide crystal form in which wet crystals of enzalutamide are obtained in a step of crystallizing in the production process of the enzalutamide crystal form, and then 2-propanol which is solvated with enzalutamide and the B-type crystals are reduced. The present invention relates to a production method of an enzalutamide crystal form, which comprises a step of crystallizing for obtaining wet crystals of enzalutamide, and a step of drying the wet crystals, and comprises a step of washing using a mixed solvent of a good solvent and a poor solvent after the step of crystallizing.

1 Claim, 4 Drawing Sheets

A-type Crystal

B-type Crystal

A-type Crystal (Enlarged)

B-type Crystal (Enlarged)

PRODUCTION METHOD OF ENZALUTAMIDE CRYSTAL FORM

TECHNICAL FIELD

The present invention relates to a novel method for producing an enzalutamide crystal form. The present invention also relates to a novel method for producing an intermediate product thereof.

BACKGROUND ART

Enzalutamide (MDV3100) is an oral androgen receptor inhibitor which is capable of preventing the growth of a castration-resistant prostate cancer promoted by androgen and is very useful.

As a form of an enzalutamide bulk drug, development of a solvent-free crystal form (hereinafter, also referred to as "A-type crystals") is in progress, but it is suggested that there is a possibility that enzalutamide is often formed as a solvate which is a solvent addition form in the process of crystallization, and the details thereof are not known (Patent Documents 1 and 2).

RELATED ART

Patent Document

[Patent Document 1] JP-T-2008-540523
[Patent Document 2] JP-T-2013-520519

DISCLOSURE OF INVENTION

Problems to be Solved by the Invention

According to the production method of enzalutamide described in Patent Document 2, 2-propanol and isopropyl acetate (IPAc) are mainly used as the final crystallization solvent. If these solvents are used, there is a possibility that in addition to the A-type crystals of enzalutamide, crystals which are 1/2 solvates of 2-propanol (hereinafter, also referred to as "B-type crystals") are mixed in. Therefore, it is necessary to go through a step of drying for a long period of time for transiting the B-type crystals to the A-type crystals. Further, it is found that transition from the A-type crystals to the B-type crystals occurs in the step of drying depending on the drying conditions, in some cases.

A problem to be solved by the present invention is to provide a novel production method of an enzalutamide crystal form in which wet crystals of enzalutamide are obtained in a step of crystallizing in the production process of the enzalutamide crystal form, and then from the wet crystals, 2-propanol itself which is solvated with enzalutamide and the B-type crystals are reduced. Further, another problem to be solved the present invention is to provide a novel production method of an enzalutamide crystal form in which other solvents which are solvated with enzalutamide and the crystal forms thereof are also examined and such other crystal forms are also reduced.

Means for Solving the Problems

The present inventors have conducted extensive studies, and as a result, they have found that, by newly including a step of washing using a specific solvent after a step of crystallizing, it is possible to produce A-type crystals of enzalutamide in which a solvate of a solvent addition form has been reduced, and completed the present invention.

That is, the present invention relates to the following <1> to <7>.

<1> A production method of an enzalutamide crystal form represented by the following formula, comprising a step of crystallizing for obtaining wet crystals of enzalutamide, and a step of drying the wet crystals, wherein the production method comprises a step of washing using a mixed solvent of a good solvent and a poor solvent after the step of crystallizing.

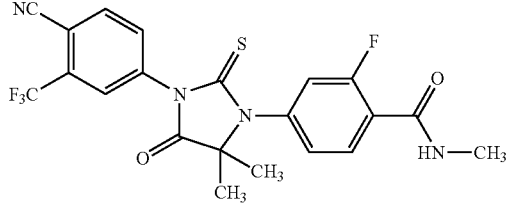

[Chem. 1]

<2> The production method of the enzalutamide crystal form described in <1> above, wherein the step of washing is performed before the step of drying.

<3> The production method of the enzalutamide crystal form described in <1> or <2> above, wherein the proportion of the good solvent and the poor solvent in the mixed solvent is 1:99 to 99:1 in volume ratio.

<4> The production method of the enzalutamide crystal form described in any one of <1> to <3> above, wherein the good solvent is at least one solvent selected from the group consisting of an acetic acid ester-based organic solvent, acetone, methyl ethyl ketone, tetrahydrofuran, and acetonitrile.

<5> The production method of the enzalutamide crystal form described in any one of <1> to <4> above, wherein the poor solvent is at least one solvent selected from the group consisting of a hydrocarbon-based organic solvent, water, and methyl-tert-butyl ether.

<6> The production method of the enzalutamide crystal form described in any one of <1> to <5> above, wherein the good solvent is isopropyl acetate and the poor solvent is n-heptane.

<7> A production method of 4-cyano-3-trifluoromethylphenyl isothiocyanate, comprising a step of dissolving thiophosgene in a mixed solvent of a hydrocarbon-based organic solvent or a chlorine-based organic solvent and water, and adding dropwise thereto a solution in which 4-cyano-3-trifluoromethyl aniline is dissolved in a hydrocarbon-based organic solvent or a chlorine-based organic solvent.

Effects of the Invention

According to the production method of an enzalutamide crystal form according to the present invention, it is possible to obtain a solvent-free enzalutamide crystal form (A-type crystals) in which crystals which are 1/2 solvates of 2-propanol of enzalutamide (B-type crystals) have been reduced, without going through a step of drying at a high temperature and for a long period of time.

Further, it is possible to obtain the A-type crystals of enzalutamide in which a crystal form of enzalutamide which is a solvate with a solvent other than 2-propanol has also been reduced.

EMBODIMENTS FOR CARRYING OUT THE INVENTION

Figure 1:
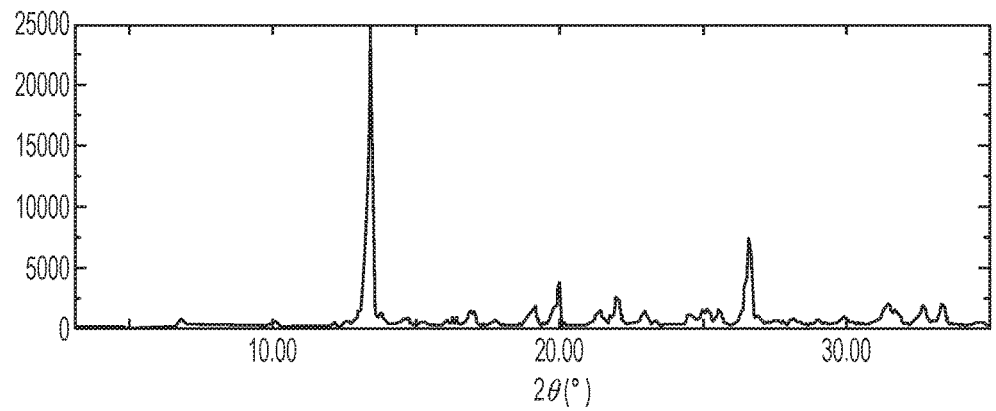
FIG. 1 is a powder X-ray diffraction spectrum of A-type crystals of enzalutamide.

Hereinafter, the present invention will be described in detail, but the present invention is not limited to the following embodiment, and any modifications can be made without departing from the gist of the present invention.

Further, in the present specification, "% by weight" and "% by mass" are the same meaning.

The present invention is a production method of an enzalutamide crystal form represented by the following formula, comprising a step of crystallizing for obtaining wet crystals of enzalutamide, and a step of drying the wet crystals, and by including a step of washing using a mixed solvent of a good solvent and a poor solvent after the step of crystallizing, it is possible to obtain a solvent-free enzalutamide crystal form (A-type crystals) in which crystals which are 1/2 solvates of 2-propanol (B-type crystals) have been reduced.

[Chem. 2]

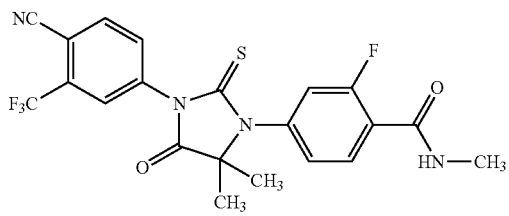 [SMILES: CNC(=O)c1ccc(N2C(=S)N(c3ccc(C#N)c(C(F)(F)F)c3)C(=O)C2(C)C)cc1F]

For example, enzalutamide can be prepared by the following reaction. That is, enzalutamide can be obtained by reacting 2-(3-fluoro-4-methylcarbamoyl-phenylamino)-2-methyl-propionic acid methyl ester (hereinafter, referred to as a "compound (A)" in some cases) and 4-cyano-3-trifluoromethylphenyl isothiocyanate (hereinafter, referred to as a "compound (B)" in some cases) in the presence of dimethyl sulfoxide (DMSO) by heating.

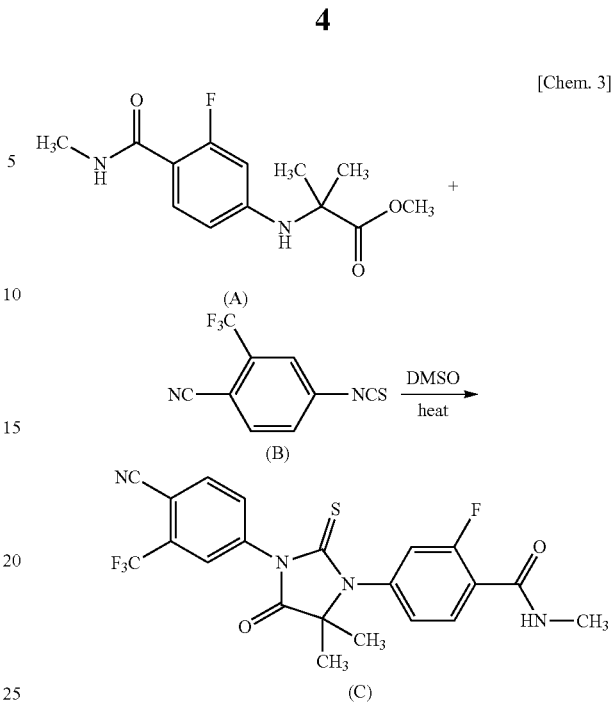

Both the compound (A) and the compound (B) can be synthesized, for example, by the known method described in Patent Document 2, but in synthesis of the compound (B), it is difficult to control impurities, in particular, dimer impurities. Thus, when the following dropping method is used instead of a method in the related art in which thiophosgene is added dropwise to a heptane-water mixed solution of 4-cyano-3-trifluoromethyl aniline, it is possible to obtain the compound (B) by favorably controlling impurities, and thus, this is more preferable.

Thiophosgene is dissolved in a mixed solvent of a hydrocarbon-based organic solvent or a chlorine-based organic solvent and water, and a solution in which 4-cyano-3-trifluoromethyl aniline is dissolved in a hydrocarbon-based organic solvent or a chlorine-based organic solvent is added dropwise thereto. Thereafter, stirring is performed at 0° C. to 30° C., and the organic layer was collected by separation. After a potassium hydrogen carbonate aqueous solution is added to the organic layer, the aqueous layer was removed, and concentration was performed. After a hydrocarbon-based organic solvent is added thereto, stirring and filtration are performed, and as a result, the compound (B) can be obtained.

Since the reaction proceeds in a two-layer system of liquid-liquid from beginning to end, and it is possible to favorably control impurities including the excessive reaction product, it is possible to obtain the compound (B) with a high yield.

As the solvent for dissolving thiophosgene, a mixed solvent of water and a hydrocarbon-based organic solvent such as hexane, an ether-based organic solvent such as ether, an acetic acid ester-based organic solvent such as ethyl acetate or isopropyl acetate, or a chlorine-based organic solvent such as methylene chloride is preferable, and a mixed solvent of water and an acetic acid ester-based organic solvent such as ethyl acetate or isopropyl acetate is more preferable.

The mixing ratio between an acetic acid ester-based solvent and water is preferably 0.1:1 to 20:1 in a volume ratio.

As the solvent of 4-cyano-3-trifluoromethyl aniline, a general hydrocarbon-based organic solvent such as hexane, an ether-based organic solvent such as ether, an acetic acid ester-based organic solvent such as ethyl acetate or isopropyl acetate, or a chlorine-based organic solvent such as methylene chloride is preferable, and an acetic acid ester-based organic solvent such as ethyl acetate or isopropyl acetate is more preferable. The concentration of an acetic acid ester-based solvent solution of 4-cyano-3-trifluoromethyl aniline is preferably 1 g/mL or less.

The dropping rate of the acetic acid ester-based solvent solution of 4-cyano-3-trifluoromethyl aniline is preferably 10 L or less per minute.

The reaction temperature after dropping is preferably −10° C. to 50° C., and more preferably 0° C. to 30° C. The reaction time is preferably 0.1 hours to 24 hours, and more preferably 1 hour or longer.

The aqueous solution to be added to the organic layer may be water or a basic aqueous solution containing a salt of sodium or potassium, and is more preferably a potassium hydrogen carbonate aqueous solution.

Instead of the hydrocarbon-based solvent to be added after the aqueous layer is removed and the concentration is performed, water may be added.

It is possible to prepare enzalutamide from the compounds (A) and (B), for example, by going through the following steps in this order:

a. a step of stirring after the compounds (A) and (B) are dissolved in a mixed solvent of DMSO and IPAc, b. a step of adding 2-propanol (IPA) dropwise, c. then, a step of collecting the organic layer by separation, d. a step of adding seed crystals of enzalutamide (A-type crystals) to the organic layer collected by separation described above, e. a step of obtaining wet crystals of enzalutamide, and f. a step of drying the wet crystals.

In the present invention, by performing a step of washing using a mixed solvent of a good solvent and a poor solvent after the step e. of obtaining wet crystals of enzalutamide in the above preparation method (hereinafter, referred to as a "step of crystallizing" in some cases), it is possible to obtain a solvent-free enzalutamide crystal form (A-type crystals) in which the B-type crystals have been reduced. In addition, if the step of washing is performed before the step of drying the wet crystals (hereinafter, referred to as a "step of drying" in some cases), the B-type crystals can be easily transited to the A-type crystals by the step of drying under mild conditions, and thus, this is preferable.

If seed crystals of the B-type crystals are present in the system, by suspending the A-type crystals in the presence of IPA, transition to the B-type crystals easily occurs even at room temperature. For this reason, there is a concern that transition from the A-type crystals to the B-type crystals occurs in all states, in the step of crystallizing or between the step of crystallizing and the step of drying, in the middle of the step of drying, or after the step of drying. Therefore, to stably obtain the A-type crystals of enzalutamide in which the B-type crystals have been reduced, it is necessary to transit the B-type crystals to the A-type crystals and remove IPA which becomes the source of the type B crystals by drying by heating under reduced pressure for a long period of time.

However, by washing wet crystals with a mixed solvent of a good solvent and a poor solvent after the crystallization step, the B-type crystals can be easily transited to the A-type crystals. Further, it is also possible to remove the residual IPA in the wet crystals which causes a transition to the type B crystals by the washing. Therefore, it is possible to prevent transition from the A-type crystals to the B-type crystals, and it is possible to obtain the A-type crystals of enzalutamide in which the B-type crystals have been completely reduced through the drying step under mild conditions, without going through a drying step at a high temperature and for a long period of time.

It is thought that the B-type crystals in the system are transited to the A-type crystals by solvent-mediated transition by using a mixed solvent of a good solvent and a poor solvent. In addition, it is thought that the IPA remaining in the wet crystals is removed as filtration washing solution by solvent substitution by the mixed solvent.

The good solvent in the mixed solvent is a solvent in which the solubility of the wet crystals is 10 g/L or more at 25° C., and preferably 30 g/L or more Specific examples thereof include an acetic acid ester-based organic solvent such as ethyl acetate or isopropyl acetate, acetone, methyl ethyl ketone, tetrahydrofuran, and acetonitrile. Among these, isopropyl acetate is preferable from the viewpoint of solubility. The good solvent may be one kind or two or more kinds.

The poor solvent in the mixed solvent is a solvent in which the solubility of the wet crystals is less than 5 g/L at 25° C., and preferably less than 1 g/L.

Specific examples thereof include a hydrocarbon-based organic solvent such as n-heptane or cyclohexane, water, and methyl-tert-butyl ether. Among these, n-heptane is preferable from the viewpoint of solubility. The poor solvent may be one kind or two or more kinds.

The proportion between the good solvent and the poor solvent is preferably 1:99 to 99:1 in volume ratio from the viewpoint of solubility, and more preferably 5:95 to 40:60, and still more preferably 25:75 to 35:65.

As a combination of the good solvent and the poor solvent, a mixed solvent in which the volume ratio between isopropyl acetate and n-heptane is 30:70 is most preferable.

In the step of washing, the wet crystals are suspended in the mixed solvent, followed by stirring. The stirring time is preferably 5 minutes or longer, more preferably 10 minutes or longer, and still more preferably 15 minutes or longer. In addition, if stirring is performed for about 1 hour as the upper limit, the B-type crystals are transited to the A-type crystals, and thus, this is sufficient.

The step of washing may be performed once, or washing may be repeatedly performed two or more times by deliquoring after washing. By repeating washing and deliquoring, it is possible to more completely perform transition from the B type crystals to the A type crystals and removal of IPA remaining.

Heating is not required during stirring, and the temperature is preferably 0° C. to 40° C. and more preferably 5° C. to 30° C.

After the step of washing, the step of drying is preferably performed.

In the step of drying, drying under reduced pressure is preferably performed at an external temperature of 25° C. to 65° C., and more preferably at an external temperature of 45° C. to 55° C. The drying time is preferably 1 hour to 68 hours.

Moreover, even in a case where the step of washing using the mixed solvent is performed, or instead of the step of washing, the mixed solvent of the good solvent and the poor solvent instead of IPA is used as the solvent used in the step of crystallizing, it is possible to obtain the desired A-type crystals of enzalutamide.

As the crystal form of enzalutamide, in addition to solvent-free A-type crystals and the B type crystals which are 1/2 solvates of 2-propanol, depending on the solvent used, C-type crystals which are 1/2 solvates of methanol, D-type crystals which are monosolvates of dioxane, E-type crystals which are 1/2 solvates of dioxane, and F-type crystals which are monosolvates of dimethyl sulfoxide are present.

For these C-type crystals to E-type crystals, by performing suspending-purification using a mixed solvent of a good solvent and a poor solvent in the same manner as in the B-type crystals, the C-type crystals to the E-type crystals can be transited to the A-type crystals. In addition, it is possible to remove solvents constituting the C-type crystals to the E-type crystals, that is, methanol and dioxane from the wet crystals.

Moreover, as a mixed solvent in the step of washing used when obtaining the A-type crystals of enzalutamide in which the C-type crystals to the E-type crystals have been reduced, the same solvent as the mixed solvent used for reducing the B-type crystals can be used.

The identification of the A-type crystals, the B-type crystals, and the C-type crystals to the F-type crystals of enzalutamide can be performed by $^1$H-NMR, elemental analysis, and powder X-ray diffractometry (XRD), and the thermal properties can be confirmed by differential scanning calorimetry (DSC).

EXAMPLES

Hereinafter, the present invention will be specifically described with reference to Examples, but the present invention is not limited thereto.

<Evaluation Method>

In these examples, $^1$H-NMR measurement by a nuclear magnetic resonance apparatus (JNM-ECS400, manufactured by JEOL, Ltd., 400 MHz), XRD measurement by a powder X-ray diffraction apparatus, (Miniflex, manufactured by Rigaku Corporation), measurement by an elemental analysis apparatus (Micro cube manufactured by Elementar Analysensysteme GmbH and ion chromatogram ICS-3000 manufactured by Thermo Fisher Scientific Inc.), and DSC measurement by a differential scanning calorimeter (Q2000 V24.4 Build 116, manufactured by Ta Instruments) were performed on the obtained crystal form.

As the solvent of $^1$H-NMR, DMSO-$d_6$ was used for A-type crystals to E-type crystals, and CDCl$_3$-$d_6$ was used for F-type crystals.

The conditions of the XRD measurement were as follows.

X-ray: CuKα, voltage-current: 30 kV-15 mA, measuring range: 2θ=0° to 35°, scan speed: 2°/min, divergence slit width: variable, scattering slit width: 4.2°, photoreception slit width: 0.3 mm, measurement error: ±0.5°

The conditions of the DSC measurement were as follows.

Temperature range: 20° C. to 230° C., sweep rate: 10° C./min, measurement atmosphere: N$_2$ gas (40 mL/min), sample pan made of stainless steel, completely sealed.

(Example 1) Synthesis of 4-cyano-3-trifluoromethylphenyl isothiocyanate

A isopropyl acetate (IPAc) (20 mL)/aqueous solution (56 mL) of thiophosgene (14.9 g) was prepared, and a solution obtained by dissolving 4-cyano-3-trifluoromethylaniline (20 g) in an IPAc solution (90 mL) was added dropwise thereto over a period of 30 minutes. The internal temperature was 4° C. After stirring for 5 minutes at the internal temperature of 4° C., the resultant product was allowed to stand for 30 minutes or longer, and the aqueous layer was separated. The obtained organic layer was concentrated under reduced pressure, then, n-heptane was added to the concentrated residue, and was further concentrated under reduced pressure so as to be 80 mL or less. IPAc (1 mL) was added to the obtained concentrated residue and the resultant product was stirred at an internal temperature of 40° C. for 5 minutes. Seed crystals (10 mg) were added thereto at 25° C., then, stirring was performed for 1 hour, followed by stirring at an internal temperature of 4° C. and filtration, to obtain 4-cyano-3-trifluoromethylphenyl isothiocyanate (22.1 g).

(Example 2) Synthesis of Enzalutamide A-type Crystals

In a nitrogen atmosphere, 2-(3-fluoro-4-methylcarbamoyl-phenylamino)-2-methyl-propionic acid methyl ester (33.0 g) and the 4-cyano-3-trifluoromethylphenyl isothiocyanate (56.1 g) obtained in Example 1 were dissolved in a mixed solvent of dimethyl sulfoxide (DMSO) (33 mL) and IPAc (66 mL), then, the internal temperature was raised to 75° C. to 85° C., followed by stirring at the same temperature for 12 hours or longer. After the reaction ended, methanol (4.95 mL) was added dropwise thereto at 55° C. to 80° C., and the resultant product was stirred at the same temperature for 60 minutes to 90 minutes. Thereafter, after cooling to 15° C. to 25° C., the resultant product was diluted with IPAc (198 mL) and purified water (99 mL), then, stirred at the same temperature for 10 minutes to 30 minutes, and was allowed to stand for 30 minutes to 45 minutes. 2-Propanol (IPA) (49.5 mL) was added slowly dropwise thereto at an internal temperature of 15° C. to 25° C. to destroy the emulsion. The organic layer was collected by separation, and the line was washed with IPAc (15 mL).

The separated organic layer was concentrated under reduced pressure such that the amount of the solution became about 165 mL. The solution after the concentration was heated to 80° C. to 85° C., and was stirred at the same temperature for 30 minutes to 60 minutes to completely dissolve the suspension.

IPA (330 mL) subjected to clarifying filtration at 60° C. to 70° C. in advance was added to the solution after the concentration while maintaining the temperature at 70° C. or higher. Concentration was performed under ordinary pressure such that the amount of the solution became about 660 mL. IPA (165 mL) subjected to clarifying filtration at 60° C. to 70° C. in advance was added to the solution after the concentration while maintaining the temperature at 70° C. or higher. Concentration was performed under ordinary pressure such that the amount of the solution thereof became about 264 mL.

The internal temperature was adjusted to 75° C. to 85° C., and seed crystals were added thereto, followed by cooling to an internal temperature of 55° C. to 65° C. at 10° C./hour to 20° C./hour, and stirring at the same temperature for 30 minutes to 60 minutes. Then, the resultant product was cooled to an internal temperature of 0° C. to 10° C. at 10° C./hour to 20° C./hour. After confirming that the inner temperature reached 0° C. to 10° C., the slurry was filtered and washed with IPA (138 mL). This operation was performed twice.

Then, a solution (about 99 mL) of IPAc/n-heptane=3:7 (volume ratio) prepared in advance was put thereinto, followed by stirring at 5° C. to 30° C. for 10 minutes. After stirring ended, deliquoring was performed. This operation was performed twice. Further, a solution (about 165 mL) of IPAc/n-heptane=3:7 (volume ratio) prepared in advance was put thereinto, followed by stirring at 20° C. to 30° C. for 1 hour or longer. After stirring ended, deliquoring was performed, and the obtained crystals were dried under reduced pressure at an external temperature of 45° C. to 55° C. for 240 minutes. The obtained A-type crystals of enzalutamide were 45.79 g and the yield was 80.2%.

The results of $^1$H-NMR of the obtained A-type crystals are shown below, the results of elemental analysis of the obtained A-type crystals are shown in Table 1, the results of an XRD measurement of the obtained A-type crystals are shown in FIG. 1, and the values of 2θ of the peak tops of the XRD spectrum of the obtained A-type crystals are shown below, respectively. In addition, in DSC analysis, an endothermic peak was observed near 200° C.

$^1$H-NMR (DMSO-$d_6$, 400 MHz):δ(ppm)=1.55 (6H,s), 2.81 (3H,d,J=4.8 Hz),7.34 (1H),7.43 (1H),7.79 (1H),8.09 (1H),8.30 (1H),8.41 (1H),8.46 (1H) XRD:2θ(°)=13.2,16.7, 18.9,19.8,21.2,21.8,25.4,26.4

TABLE 1

| | Element | | | | | |
|---|---|---|---|---|---|---|
| | C | H | N | O | S | F |
| Theoretical value | 54.31 | 3.47 | 12.06 | 6.89 | 6.90 | 16.36 |
| Measured value | 54.21 | 3.44 | 12.04 | — | 6.89 | 16.31 |

(Reference Example 1-1) Synthesis of Enzalutamide B-type Crystals

In a nitrogen atmosphere, a solution of fine crystals (10.0 g) of the enzalutamide A type crystals in IPA (80 mL) was stirred at room temperature. Seed crystals (10.2 mg=0.1% by mass) of enzalutamide B-type crystals were added thereto at 20° C. to 30° C., followed by stirring at the same temperature for 4 days. After stirring, the precipitated crystals were collected by filtration. Thereafter, the precipitated crystals were washed with IPA (10 mL), and dried under reduced pressure at 55° C. for about 4 hours, to obtain 10.3 g of enzalutamide B-type crystals which are 1/2 solvates of IPA. The yield was 96.2%

Figure 2:
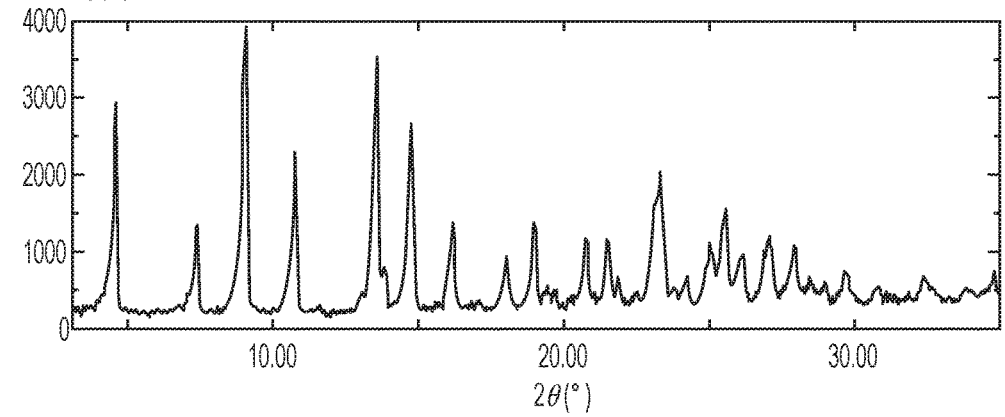
FIG. 2 is a powder X-ray diffraction spectrum of B-type crystals of enzalutamide.

The results of $^1$H-NMR of the obtained B-type crystals are shown below, the results of elemental analysis of the obtained B-type crystals are shown in Table 2, the results of an XRD measurement of the obtained B-type crystals are shown in FIG. 2, and the values of 2θ of the peak tops of the XRD spectrum of the obtained B-type crystals are shown below, respectively. In addition, in DSC analysis, endothermic peaks were observed near 109° C. and 200° C.

$^1$H-NMR (DMSO-$d_6$, 400 MHz):δ(ppm)=1.04 (3H,d, J=6.0 Hz),1.55 (6H,s),2.81 (3H,d,J=4.8 Hz),3.77 (0.5H,m), 4. 36 (0.5H,d,J=4.4 Hz),7.34 (1H),7.43 (1H),7.79 (1H),8.09 (1H),8.30 (1H),8.41 (1H),8.46 (1H) XRD:2θ(°)=4.6,7.4,9.1, 10.8,13.6,14.8,16.2,20.9,23.4,25.6

TABLE 2

| | Element | | | | | |
|---|---|---|---|---|---|---|
| | C | H | N | O | S | F |
| Theoretical value | 54.65 | 4.08 | 11.33 | 8.09 | 6.48 | 15.37 |
| Measured value | 54.50 | 4.10 | 11.31 | — | 6.48 | 15.37 |

(Example 3) Transition from Enzalutamide B-type Crystals to A-type Crystals

In a nitrogen atmosphere, a mixed solution of isopropyl acetate (3.0 mL) which is a good solvent and n-heptane (7.0 mL) which is a poor solvent, for the enzalutamide B-type crystals (2.0 g), was stirred at an internal temperature of 20° C. to 30° C. for 1 hour or longer. After stirring, the precipitated crystals were collected by filtration, and washed with n-heptane (4.0 mL). The obtained crystals were dried under reduced pressure at 55° C. for 3 hours, whereby A-type crystals of enzalutamide were obtained.

Figure 7:
FIG. 7 shows scanning electron microscope images of the A-type crystals and the B-type crystals of enzalutamide.
Figure 7:
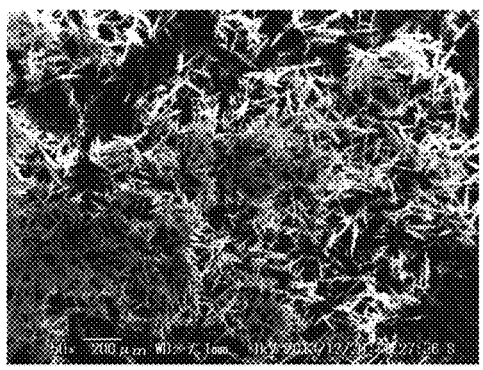
Figure 7:
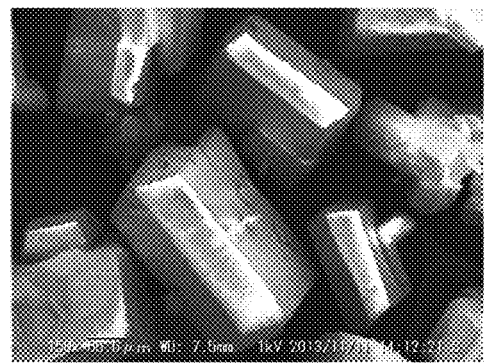
Figure 7:
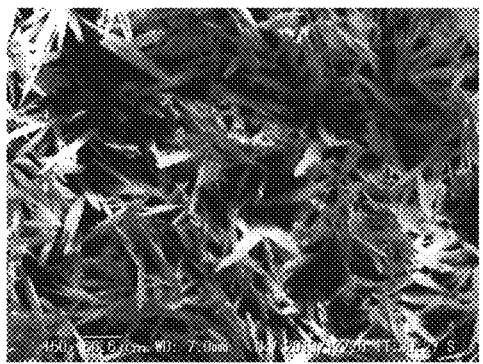

Scanning electron microscope images of the obtained A-type crystals and the B-type crystals of enzalutamide are shown in FIG. 7. From this, it was found that, while the solvent-free A-type crystals were cubic crystals, the B-type crystals which are 1/2 solvates of IPA were needle crystals.

(Reference Example 1-2) Time Dependence of Step of Washing

A-type crystals of enzalutamide were obtained in the same manner as above (Example 3) except that the stirring time of the mixed solution of isopropyl acetate (3.0 mL) which is a good solvent and n-heptane (7.0 mL) which is a poor solvent were changed to 1 minute, 5 minutes, 15 minutes, 30 minutes, or 1 hour.

In the XRD spectrum of the obtained crystals, from each integral value of the peak derived from the A-type crystals and the peak derived from IPA, the content of IPA and the presence ratio of A-type crystals and the B-type crystals were determined. Here, since the B-type crystals are 1/2 solvates of IPA, the content of IPA corresponds to 1/2 mole equivalents of the content of the B-type crystals. The results are shown in Table 3. From this, even in a case where a step of washing using the mixed solvent of the good solvent and the poor solvent was performed for 1 minute, it was found that transition from the type B crystals to the A-type crystals of enzalutamide occurs. In addition, if the step of washing was performed for 5 minutes or longer, 95% or greater of the B-type crystals was transited to the A-type crystals, and if the step of washing was performed for 15 minutes or longer, the B-type crystals were completely transited to the A-type crystals. Moreover, "N.D." in Table 3 indicates that the content was not detected.

TABLE 3

| Stirring time | IPA content | A-type crystals:B-type crystals |
|---|---|---|
| — (in a case where B-type crystals are 100%) | 60770 ppm | 0:100 |
| 1 minute | 26980 ppm | 55.6:44.4 |
| 5 minutes | 2672 ppm | 95.6:4.4 |
| 15 minutes | N.D. | 100:0 |
| 30 minutes | N.D. | 100:0 |
| 1 hour | N.D. | 100:0 |

(Reference Example 2) Synthesis of Enzalutamide C-type Crystals

In a nitrogen atmosphere, a solution of fine crystals (10.0 g) of the enzalutamide A type crystals in methanol (45 mL) was heated to an internal temperature of 50° C. to 60° C., and stirred at the same temperature for 15 minutes. After stirring, n-heptane (105 mL) was added dropwise thereto at an internal temperature of near 50° C. over a period of 45 minutes, followed by stirring at the same temperature for 15 minutes or longer. After stirring, the resultant product was cooled to an internal temperature of 20° C. to 30° C., and stirred at the same temperature overnight. To obtain the precipitated precipitate, decantation was performed, and concentration under reduced pressure was performed at 40° C. or lower, whereby the solvent was completely removed.

The obtained crystals were dried under reduced pressure at room temperature, whereby 8.86 g of enzalutamide C-type crystals which are ½ solvates of methanol were obtained. The yield was 86.0%.

Figure 3:
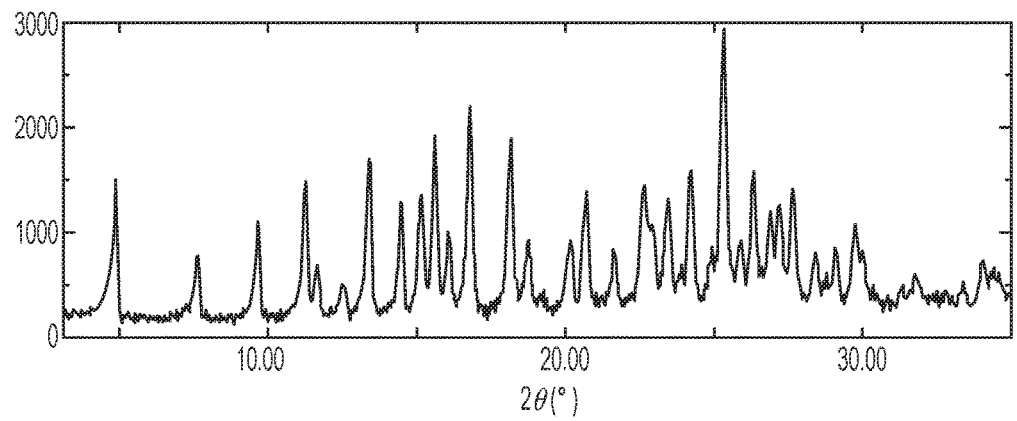
FIG. 3 is a powder X-ray diffraction spectrum of C-type crystals of enzalutamide.

The results of $^1$H-NMR of the obtained C-type crystals are shown below, the results of elemental analysis of the obtained C-type crystals are shown in Table 4, the results of an XRD measurement of the obtained C-type crystals are shown in FIG. 3, and the values of 2θ of the peak tops of the XRD spectrum of the obtained C-type crystals are shown below, respectively. In addition, in DSC analysis, endothermic peaks were observed near 137° C., 142° C., and 200° C.

$^1$H-NMR (DMSO-$d_6$, 400 MHz):δ(ppm)=1.55(6H,s),2.81 (3H,d,J=4.8 Hz),3.17(1.5H,d,J=5.2 Hz),4.11(0.5H,q,J=5.2 Hz),7.34 (1H),7.43 (1H),7.79 (1H),8.09 (1H),8.30 (1H),8.41 (1H),8.46 (1H) XRD:2θ(°)=4.8,9.6,11.2,13.8,15.8,16.7, 18.1,22.6,24.2,25.4

TABLE 4

| | Element | | | | | |
|---|---|---|---|---|---|---|
| | C | H | N | O | S | F |
| Theoretical value | 53.75 | 3.78 | 11.66 | 8.33 | 6.67 | 15.82 |
| Measured value | 53.43 | 3.74 | 11.75 | — | 6.72 | 15.87 |

(Example 4) Transition from Enzalutamide C-type Crystal to A-type Crystal

In a nitrogen atmosphere, a mixed solution of isopropyl acetate (0.45 mL) which is a good solvent and n-heptane (1.05 mL) which is a poor solvent, for the enzalutamide C-type crystals (0.3 g), was stirred at an internal temperature of 50° C. to 60° C. for 1 hour or longer. After stirring, the resultant product was cooled to an internal temperature of 20° C. to 30° C., and stirred at the same temperature for 30 minutes or longer. The precipitated crystals were collected by filtration, and washed with n-heptane (1.0 mL). The obtained crystals were dried under reduced pressure at 25° C. for 4 hours, whereby A-type crystals of enzalutamide were obtained.

(Reference Example 3) Synthesis of Enzalutamide D-type Crystals

In a nitrogen atmosphere, a solution of fine crystals (6.0 g) of the enzalutamide A type crystals in dioxane (30 mL) was heated to an internal temperature of near 70° C., and dissolution was confirmed. After confirming dissolution, the resultant product was slowly cooled to near 15° C. At this time, precipitation of crystals was observed near 20° C. The resultant product was stirred at an internal temperature of 15° C. overnight, and the precipitated crystals were collected by filtration. Thereafter, the precipitated crystals were washed with dioxane (6 mL), and dried under reduced pressure at room temperature for 1 hour, whereby 4.72 g of enzalutamide D-type crystals which were monosolvates of dioxane were obtained. The yield was 66.1%.

Figure 4:
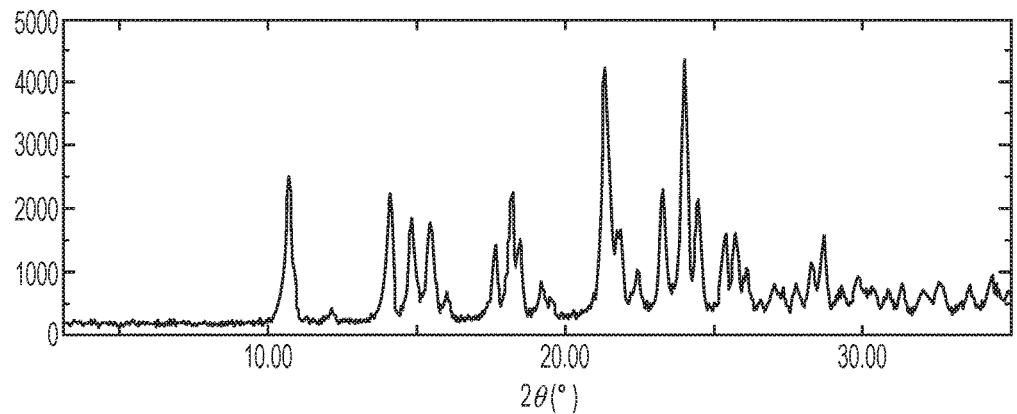
FIG. 4 is a powder X-ray diffraction spectrum of D-type crystals of enzalutamide.

The results of $^1$H-NMR of the obtained D-type crystals are shown below, the results of elemental analysis of the obtained D-type crystals are shown in Table 5, the results of an XRD measurement of the obtained D-type crystals are shown in FIG. 4, and the values of 2θ of the peak tops of the XRD spectrum of the obtained D-type crystals are shown below, respectively.

$^1$H-NMR (DMSO-$d_6$,400 MHz):δ(ppm)=1.55 (6H,s),2.81 (3H,d,J=4.8 Hz),3.57 (8H,s),7.34 (1H),7.43 (1H),7.79 (1H), 8.09 (1H),8.30 (1H),8.41 (1H),8.46 (1H) XRD:2θ(°)=10.7, 14.1,14.8,15.4,18.2,21.4,24.1

TABLE 5

| | Element | | | | | |
|---|---|---|---|---|---|---|
| | C | H | N | O | S | F |
| Theoretical value | 54.34 | 4.38 | 10.14 | 11.58 | 5.80 | 13.75 |
| Measured value | 54.25 | 4.40 | 10.33 | — | 5.91 | 14.04 |

(Example 5) Transition from Enzalutamide D-type Crystals to A-type Crystals

In a nitrogen atmosphere, a mixed solution of isopropyl acetate (0.45 mL) which is a good solvent and n-heptane (1.05 mL) which is a poor solvent, for the enzalutamide D-type crystals (0.3 g), was stirred at an internal temperature of 70° C. to 80° C. for 1 hour or longer. After stirring, the resultant product was cooled to an internal temperature of 20° C. to 30° C., and stirred at the same temperature for 30 minutes or longer. The precipitated crystals were collected by filtration, and washed with n-heptane (1.0 mL). The obtained crystals were dried under reduced pressure at 25° C. for 2 hours, whereby A-type crystals of enzalutamide were obtained.

(Reference Example 4) Synthesis of Enzalutamide E-type Crystals

In a nitrogen atmosphere, a solution of fine crystals (10.0 g) of the enzalutamide A type crystals in dioxane (30 mL) was heated to an internal temperature of 55° C., and stirred at the same temperature. After stirring, n-heptane (70 mL) was added dropwise thereto at an internal temperature of 50° C. to 60° C. over a period of 45 minutes or longer. After the dropping ended, the resultant product was cooled to an internal temperature of 20° C. to 30° C., and stirred at the same temperature overnight. After stirring, the precipitated crystals were collected by filtration. The precipitated crystals were washed with n-heptane, and dried under reduced pressure at room temperature for 2 hours, whereby 10.71 g of enzalutamide E-type crystals which were ½ solvates of dioxane were obtained. The yield was 97.8%.

Figure 5:
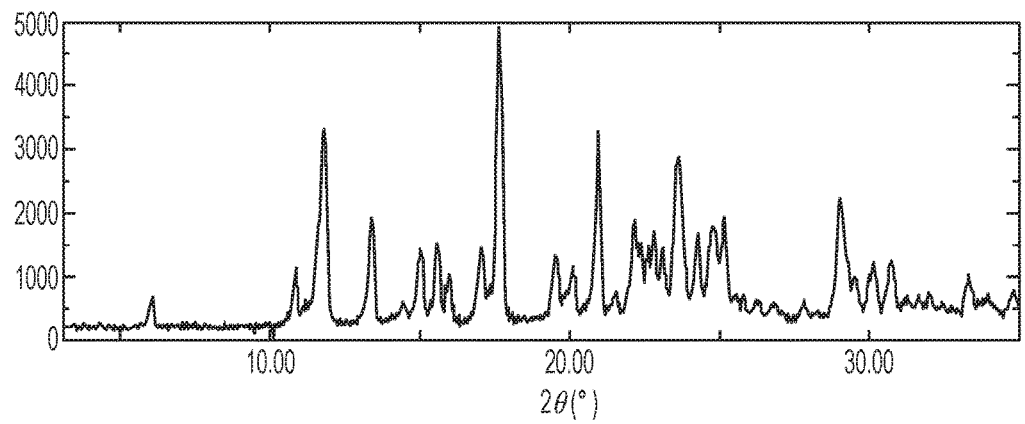
FIG. 5 is a powder X-ray diffraction spectrum of E-type crystals of enzalutamide.

The results of $^1$H-NMR of the obtained E-type crystals are shown below, the results of elemental analysis of the obtained E-type crystals are shown in Table 6, the results of an XRD measurement of the obtained E-type crystals are shown in FIG. 5, and the values of 2θ of the peak tops of the XRD spectrum of the obtained E-type crystals are shown below, respectively. In addition, in DSC analysis, endothermic peaks were observed near 118° C. and 200° C.

$^1$H-NMR (DMSO-$d_6$,400 MHz):δ(ppm)=1.55 (6H,s),2.80 (3H,d,J=4.8 Hz),3.57 (4H,s),7.34 (1H),7.43 (1H),7.79 (1H), 8.09 (1H),8.30 (1H),8.41 (1H),8.46 (1H) XRD:2θ(°)=11.7, 13.3,17.5,20.9,23.6,29.0

TABLE 6

| | Element | | | | | |
|---|---|---|---|---|---|---|
| | C | H | N | O | S | F |
| Theoretical value | 54.33 | 3.96 | 11.02 | 9.44 | 6.31 | 14.94 |
| Measured value | 54.32 | 4.02 | 11.00 | — | 6.27 | 14.93 |

(Example 6) Transition from Enzalutamide E-type Crystal to A-type Crystal

In a nitrogen atmosphere, a mixed solution of isopropyl acetate which is a good solvent and n-heptane which is a poor solvent, for the enzalutamide E-type crystals (0.2 g), was stirred at an internal temperature of 70° C. to 80° C. for 1 hour or longer. After stirring, the resultant product was cooled to an internal temperature of 20° C. to 30° C., and stirred at the same temperature for 30 minutes or longer. The precipitated crystals were collected by filtration, and washed with n-heptane (1.0 mL). The obtained crystals were dried under reduced pressure at 25° C. for 4 hours, whereby A-type crystals of enzalutamide were obtained.

(Reference Example 5) Synthesis of Enzalutamide F-type Crystal

In a nitrogen atmosphere, a solution of fine crystals (30.0 g) of the enzalutamide A type crystals in DMSO (30 mL) was heated to an internal temperature of near 100° C., and dissolution of the crystals was confirmed. After confirming dissolution, the resultant product was cooled to an internal temperature of near 40° C., and precipitation of crystals was confirmed. Then, the resultant product was cooled to an internal temperature of near 25° C., and stirred at the same temperature for 1 hour. The precipitated crystals were collected by filtration at the same temperature, and washed with DMSO (40 mL). The obtained wet crystals were dried under reduced pressure at 55° C. overnight, whereby 7.2 g of enzalutamide F-type crystals which are monosolvates of DMSO were obtained. The yield was 20.5%.

Figure 6:
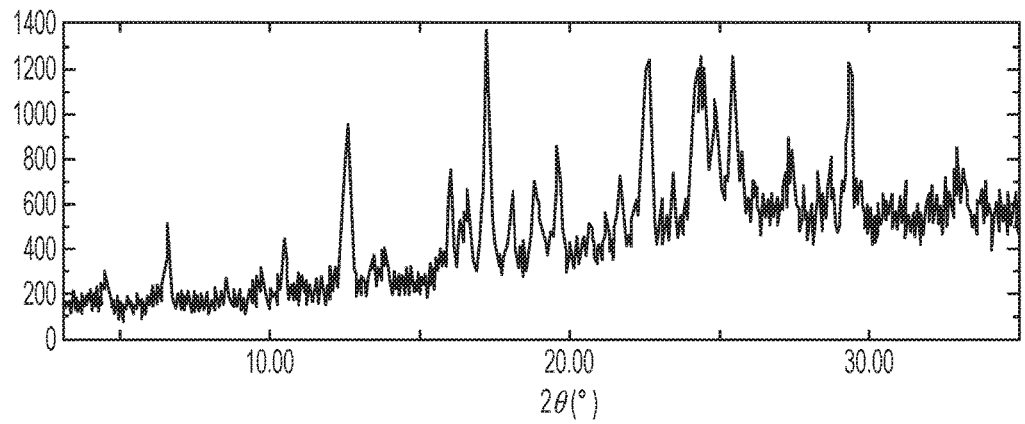
FIG. 6 is a powder X-ray diffraction spectrum of F-type crystals of enzalutamide.

The results of $^1$H-NMR of the obtained F-type crystals are shown below, the results of elemental analysis of the obtained F-type crystals are shown in Table 7, the results of an XRD measurement of the obtained F-type crystals are shown in FIG. 6, and the values of 2θ of the peak tops of the XRD spectrum of the obtained F-type crystals are shown below, respectively.

$^1$H-NMR (CDCl$_3$-d$_6$,400 MHz):δ(ppm)=1.62 (6H,s),2.62 (6H,s),3.07 (3H,d,J=4.4 Hz),6.74 (1H,m),7.15 (1H),7.2 5 (1H),7.83 (1H),7.95 (1H),7.99 (1H),8.28 (1H) XRD:2θ(°)=17.1,20.2,24.6

TABLE 7

| | Element | | | | | |
|---|---|---|---|---|---|---|
| | C | H | N | O | S | F |
| Theoretical value | 50.91 | 4.09 | 10.33 | 8.85 | 11.82 | 14.01 |
| Measured value | 50.41 | 4.15 | 10.19 | — | 11.85 | 13.81 |

While the present invention has been described in detail and with reference to specific embodiments thereof, it will be apparent to one skilled in the art that various changes and modifications can be made therein without departing from the spirit and scope thereof. The present application is based on Japanese Patent Application No. 2015-109805 filed on May 29, 2015, and the contents are incorporated herein by reference.

INDUSTRIAL APPLICABILITY

According to the present invention, it is possible to obtain solvent-free crystals of enzalutamide in which solvated crystals have been reduced under mild conditions.

The invention claimed is:

1. A method of producing a crystal form of enzalutamide:

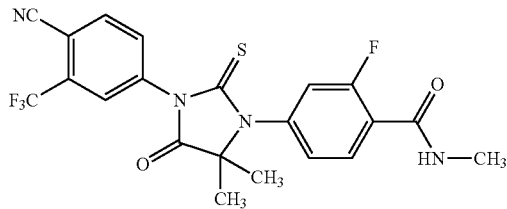

comprising a step of crysallizing for obtaining wet crystals of enzalutamide and a step of drying the wet crystals, wherein the method comprises a step of washing using a mixed solvent of a good solvent and a poor solvent after the step of crystallizing, wherein the good solvent is isopropyl acetate and the poor solvent is n-heptane.

* * * * *